Figure 1:
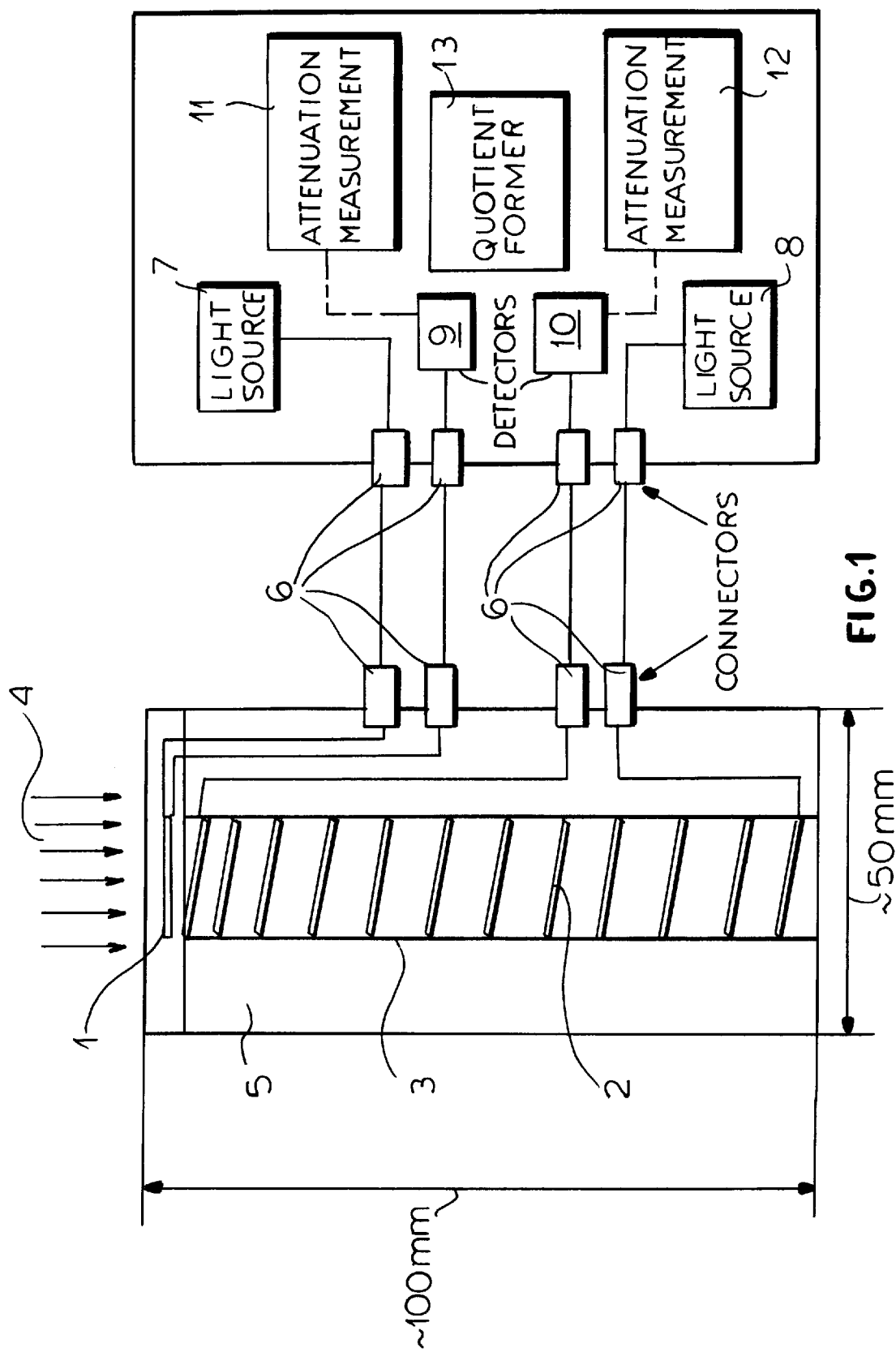

United States Patent
Gripp et al.

[11] Patent Number: 6,087,664
[45] Date of Patent: Jul. 11, 2000

[54] PROCESS AND DEVICE FOR MEASURING THE RADIATION DEPTH OF RADIATION

[75] Inventors: Stefan Gripp, Langenfeld; Friedrich-Wolfgang Häsing; Harald Büker, both of Jülich, all of Germany

[73] Assignee: Forschungszentrum Julich GmbH, Julich, Germany

[21] Appl. No.: 09/011,399

[22] PCT Filed: Jul. 25, 1996

[86] PCT No.: PCT/DE96/01405

§ 371 Date: Jan. 29, 1998

§ 102(e) Date: Jan. 29, 1998

[87] PCT Pub. No.: WO97/05506

PCT Pub. Date: Feb. 13, 1997

[30] Foreign Application Priority Data

Aug. 1, 1995 [DE] Germany ............... 195 28 096

[51] Int. Cl.[7] .............. G01T 1/17; G01T 1/185; G01T 1/20
[52] U.S. Cl. ............ 250/394; 250/363.01; 250/367; 250/366; 250/385.1
[58] Field of Search ............... 250/363.01, 366, 250/367, 385.1, 394

[56] References Cited

U.S. PATENT DOCUMENTS 4,267,446   5/1981   Brown et al. .................. 250/394

FOREIGN PATENT DOCUMENTS 2 200 984   8/1988   United Kingdom .

OTHER PUBLICATIONS

Conception of an Ionising Radiation Detection Scheme Based on Controlled Light Induced Annealing of Silica Fibres, by Vassilopoulos et al., 8049j IEE Proceedings–J 140(1993) Aug., No. 4, Part J, pp. 267–272.

*Primary Examiner*—Constantine Hannaher
*Assistant Examiner*—Andrew Israel
*Attorney, Agent, or Firm*—Herbert Dubno

[57] ABSTRACT

The invention pertains to a measurement device comprising two sensors for measuring radiation doses. The sensors are, for example, optical waveguides aligned along a straight line. One of the optical waveguides covers a longer section along the line than the other waveguide; in particular, the difference is at least 20 mm. Measurement using the measurement device is done as follows: the radiation dose along the line of radiation down to the expected penetration depth is measured using the wider sensor; the narrower sensor is used to determine the radiation dose in a volume element within the radiation path. A quotient is formed from the two measurements and used to calculate the radiation depth on the basis of reference values. The proposed device facilitates rapid and simple determination of a penetration depth of an ionizing radiation, for example in tissue.

3 Claims, 2 Drawing Sheets

PROCESS AND DEVICE FOR MEASURING THE RADIATION DEPTH OF RADIATION

CROSS REFERENCE TO RELATED APPLICATIONS

This application is a national stage of PCT/DE96/01405 filed Feb. 1, 1998 and based upon German national application 195 28 096.2 of Aug. 1, 1995 under the International Convention.

FIELD OF THE INVENTION

The invention relates to a process for measuring the radiation depth or penetration of a radiation and to a measuring device, comprised of two sensors, for measuring the radiation dose.

BACKGROUND OF THE INVENTION

It is known to determine the energy of an electron beam by measuring the penetration depth of the radiation in an object with an ionization chamber or with an arrangement of a plurality of ionization chambers. This process is time consuming and expensive from a measurement technology point of view.

A measurement device comprised of two sensors for measuring radiation dose is also known from German Patent application Ser. No. 195 03 647.6-33. This however is not provided for the measurement of penetration depth but rather for the measurement of a tissue equivalent dose.

OBJECT OF THE INVENTION

The object of the invention is to provide a process for the rapid and simple measurement of the penetration depth of an (ionizing) radiation as well as the provision of a device for carrying out the process.

SUMMARY OF THE INVENTION

According to the invention, the radiation depth is measured by measuring the radiation dose along a radiation path up to its penetration depth, measuring the radiation dose in a volume element within the radiation path forming a dose independent quotient of both measurements and determining the penetration depth of the radiation quotient based upon reference values.

Both sensors can have a three-dimensional extent parallel to or along a straight line and one of the sensors can encompass a longer stretch along the line than the other sensor. The difference in the stretches can amount to at least 20 mm.

For carrying out the process, the radiation dose is measured (in an object) along the radiation path up to the penetration depth. It is sufficient to limit the measurement to a stretch at the end of the radiation path. It is thus not required to fully pick up the radiation. Furthermore, the radiation dose is measured in a volume element located within the radiation path. So that no artifacts are detected based upon intensity fluctuations of the radiation, it is advantageous to carry out this and the aforedescribed measurement simultaneously.

Advantageously, the measurements are carried out with sensors of the same type to obtain a dose independent value upon quotient formation. Otherwise, approximations must be taken into consideration, or compensation calculations must be carried out.

In conjunction with the two measurements, a dose-independent quotient is formed from both measured values.

Based upon reference values, the penetration depth of the radiation in the object can be finally determined.

The penetration depth is a measurement of the energy of the radiation. As a consequence, the process enables determination of the energy of a radiation beam of high energy corpuscular radiation (e.g. electrons, protons, ions, neutrons). The process is suitable, inter alia, for routine monitoring of the energy of an electron beam used in radiation therapy in an energy range between 2 an 25 MeV.

A measuring device for carrying out the process is comprised of two sensors (1), (2) for measurement of the radiation dose. These have a three dimensional range which is oriented parallel to or along a straight line. One ("long") sensor (2) covers a longer stretch along the line than the other ("short") sensor (1).

The purpose of this arrangement is that radiation which runs parallel to the line is registered by the sensors upon suitable positioning of the device in the radiation path. It is then important that the longer sensor (2), by contrast to the shorter sensor (1), register the radiation up to its penetration depth. Furthermore, upon a suitable positioning in the radiation path, a sufficiently different sensor signal should be generated between the shorter sensor (1) and the longer sensor (2). The length difference or the difference with respect to the covered stretches parallel to the line are selected in accordance with these requirements. The requirements are satisfied with great differences. It has been found that, for example, a length difference of at least 20 millimeters (especially with electron radiation) should be provided to satisfy the aforementioned requirement. Shorter length differences are possible only with higher resolutions of the sensors. Preferably the length difference is 40 mm and more.

Advantageously the shorter sensor (1) covers a range of less than 10 mm in depth and the "longer" sensor a range of at least 30 mm. A sensor so dimensioned can be positioned in the requisite way in the radiation path without problems.

Radiation sensitive light waveguides, scintillation light waveguides, ionization chambers and the like are suitable as sensors.

When high sensitivity light waveguides are used (for example PbO fibers, doped with materials which have a high effective atomic number), one of the light waveguides can be oriented parallel to the beam path and the other optionally (especially perpendicular to the beam path).

When light waveguides with a reduced sensitivity are used, it is advantageous to arrange the longer sensor, in order to compensate for its reduced sensitivity, in a spiral or zig-zag form wound around the line. As a consequence, the more dense the winding the greater the measurement sensitivity. In general a sensor of reduced sensitivity, in order to compensate this deficiency, is so arranged that it covers a greater cross-section area in addition to its extent in length.

BRIEF DESCRIPTION OF THE INVENTION

The drawing shows:

FIG. 1: an embodiment of a measuring device.

Figure 2:
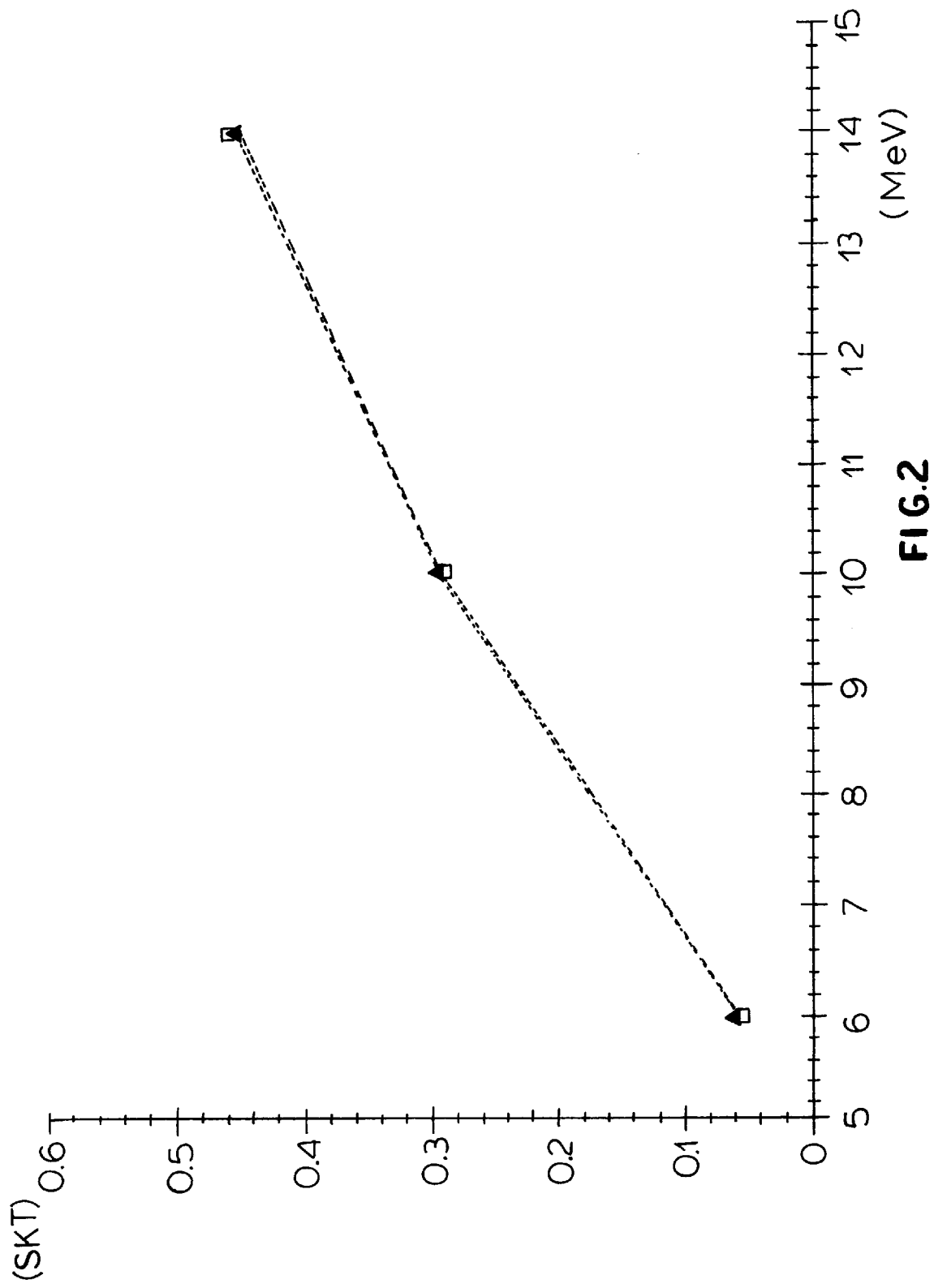

FIG. 2: results obtained in accordance with the process.

SPECIFIC DESCRIPTION

A radiation sensitive light waveguide 1 in FIG. 1 is wound in a plane around a Plexiglass cylinder 3 and a radiation sensitive light waveguide 2 is wound in spiral form around this Plexiglass cylinder 3.

As a consequence of the winding of the light waveguide 1 in a plane, its measuring signal does not depend upon the energy of the ionizing radiation or is only limitedly dependent upon the ionizing radiation if the Plexiglass cylinder 3 is positioned parallel to the radiation 4. Light waveguide 2 then extends in the depth of the measured volume (cylinders 3 and 5) so that at the waveguide 2 the measurement of the radiation induced attenuation depends strongly upon the penetration depth and thus upon the energy of the radiation. The Plexiglass cylinder 3 has a diameter of less than 25 mm and a length of 100 mm. It is located in a further outer Plexiglass cylinder 5 with a diameter of about 50 mm. By plug connectors 6, the light waveguides 1 and 2 are connected to an evaluation unit.

The evaluation unit is comprised of the light sources (LED's) 7 and 8, the detectors 9 and 10, the devices 11 and 12 for determining the attenuation, and a device 13 for calculating the penetration depth or radiation energy according to the invention. The light of the light source 7 (or 8) is supplied to the light waveguide 1 (or 2), traverses the latter and ends finally in detector 9 (or 10). By means of the detector 9 (or 10), the incoming light intensity is measured and supplied to the device 11 (or 12). By means of the device 11 (or 12) the change in the transmission of the light waveguide 1 (or 2) as a result of the incident radiation, i.e. the attenuation, is determined. By means of the device 13, the quotient of the two attenuation values of the devices 11 and 12 is formed and from the quotient, the penetration depth or radiation energy is determined. For carrying out the process, the measuring device is suitably positioned in the radiation path, i.e. the spiral of the light waveguide 2 runs along the radiation path at least to the end of the penetration depth. If, for example, a penetration depth in the range of 70 mm is expected in the object, the spiral should reach to a depth greater than 70 mm (for example 100 mm) in the object. The transmission characteristics of the light waveguides vary with incident radiation as a result of the radiation induced color centers in the material of the light waveguide. As a result, the transmission characteristics of the light waveguide vary as a function of the penetration depth of the radiation in material, (e.g. Plexiglass).

In order to use the measuring device repetitively, the light waveguides are regenerated after reaching the maximum dose load by healing of the radiation induced color centers.

The independence of the sensor signals from the applied dose, the sensor temperature and from the fading effect is achieved in that the attenuation induced in the light waveguide 2 uses the induced damping of the light waveguide 1 as a reference. If both sensor elements are composed of the same material, interference effects can be eliminated by simple quotient formation.

The resolution and measuring sensitivity of the measuring device can be varied by choice of the geometric arrangement over a wide range. Dense (spiral shaped) wound light waveguides are suitable for a high measuring sensitivity.

Other geometric arrangements (including multiple arrangements for measuring the radial or three-dimensional distribution of the electron energy) are possible.

The evaluation of the detector signals can be effected in an analog or also in a numerical manner. In analog signal processing, nonlinearities in the illustrated geometric arrangement can be eliminated by the geometry of the winding. In digital processing, such nonlinearities can be taken into consideration with a calibration curve stored in the microprocessor.

FIG. 2 shows the results obtained in accordance with the invention. Initially the radiation induced attenuation of a 100 mm long PbO sensor is measured. Experiments were carried out in which the sensor extended 28 to 82 mm in Plexiglass. With this electron radiation with an energy in the range between 6 and 14 MeV was registered. In addition, with the same (regenerated) sensor the attenuation was measured at a depth of 10 mm. The measurements were carried out for 30 seconds each. The diagram (scale parts SKT versus energy in MeV) shows the results based on the evaluation of the quotient.

What is claimed is:

1. A process for measuring radiation depth of a radiation comprising the following steps:

a) measuring a radiation dose along a radiation path up to its penetration depth;

b) measuring a radiation dose in a volume element within the radiation path;

c) forming a dose-independent quotient of both measurements; and d) determining the penetration depth of the radiation from the quotient based upon reference values.

2. A measuring device comprised of two sensors for measuring penetration depth in an absorber along a path of radiation dose, both sensors extend along said path and along a straight line such that one of the sensors extends along a longer stretch along the line than the other sensor and means for forming a quotient of measurements made by the sensors.

3. The measuring device according to claim 2 wherein the difference in the stretches of the sensors amounts to at least 20 mm.

* * * * *